United States Patent [19]

Eriksson

[11] Patent Number: 4,687,986

[45] Date of Patent: Aug. 18, 1987

[54] METHOD AND APPARATUS FOR MEASURING THE STREAMING POTENTIAL OF A PARTICLE SUSPENSION

[75] Inventor: Rune Eriksson, Mariestad, Sweden

[73] Assignee: AB Innomatic, Mariestad, Sweden

[21] Appl. No.: 875,042

[22] Filed: Jun. 17, 1986

[30] Foreign Application Priority Data

Jun. 18, 1985 [SE] Sweden .................................. 8503029
May 20, 1986 [SE] Sweden .................................. 8602280

[51] Int. Cl.$^4$ ............................................. G01N 27/00
[52] U.S. Cl. ........................................ 324/71.1; 73/63; 162/263
[58] Field of Search .................... 73/63; 162/198, 263; 324/71.1

[56] References Cited

U.S. PATENT DOCUMENTS 4,535,285 8/1985 Evans et al. ..................... 162/263 X Primary Examiner—Stewart J. Levy
Assistant Examiner—Joseph W. Roskos
Attorney, Agent, or Firm—Sughrue, Mion, Zinn, Macpeak and Seas

[57] ABSTRACT

A particle suspension from a process is introduced into a measuring vessel 1 and caused to rise above a screen 4 whereupon the streaming potential of the suspension is determined by measuring the voltage across the screen at alternately different, relatively low pressures. The measurements may be carried out continuously with the measuring vessel being rinsed between measurements. The apparatus comprises a vertical U-shaped measuring vessel 1 in which a horizontal screen plate 4 in one leg 3 defines a measuring chamber 9, the other leg 2 being supplied with the suspension. Valves V4-V8, V10 are provided to alternately subject the vessel to different measurement pressures, and to provide a high rinsing pressure. Adjacent its center the screen plate supports electrodes 5, 6 for measuring the voltages between particle suspension and filtrate, and an electrode 11 is associated with the screen plate for measuring the conductivity of the suspension. The drainage rate of the suspension may be determined by a pair of sensors 14, 15 at different levels above the screen plate and a time meter.

12 Claims, 2 Drawing Figures

METHOD AND APPARATUS FOR MEASURING THE STREAMING POTENTIAL OF A PARTICLE SUSPENSION

BACKGROUND OF THE INVENTION

In many industrial processes, such as paper making, it is of importance to know and to be able to control the relatively weak voltages which for various and as yet partly not completely understood reasons are generated in flowing particle suspensions. It has been found—see for instance the paper by W. Sack: "Kontinuierliche Stromungspotentialmessung an einer Papiermaschiene" in Das Papier 30, Nr 10A, V42-V46 (1976)—that the potentials in question may be measured by diverting from the process a sample, having the sample flow through a screen which traps most of the particles forming on the upstream side of the screen a pad of particles, and measuring, by means of two electrodes positioned on each side of the screen, the voltage differential between the upstream and the downstream side of the screen, viz. the voltage generated in the pad of particles when the liquid flows through the pad. The invention relates to a method and an appartus for carrying out measurements of this kind or for carrying out measurements of the streaming potential and/or the state of drainage of a particle suspension.

In the above paper by Sack there are also described a method and a device for measuring the streaming potential of a particle suspension. However, the apparatus is of an experimental nature intended, in the first place, for the study of the technique in question and is not suited for the highly continuous measurements required at reasonable costs for the control of the streaming potential desired in an industrial process. EP No. 0 079 726 A1 discloses an apparatus for carrying out measurements partly on the basis of and according to the contents of the above paper. Neither does this apparatus satisfactorily provide for continuous measurement as it is not, to a desirable degree, exempt from the effects of electrical disturbances, and it is unnecessarily complicated because it requires a special pump and measurements of the pressure caused by this pump. Also, it has the disadvantage that it does not permit the satisfactory disposal of waste in connection with the necessary rinsing operations.

It is a known fact that the streaming potential is proportional to the dielectric constant of the liquid phase, the pressure differential between the upstream and downstream sides of the above-mentioned particle pad, the specific conductivity of the liquid phase, and the viscosity of the liquid phase. It is also a known fact that the streaming potential and the drainage property affect each other, and hence it would be of advantage to be able to measure both simultaneously to allow the streaming potential to be corrected for the state of drainage and vice versa.

SUMMARY OF THE INVENTION

The invention, therefor, has for its purpose the provision of a method and an apparatus for measuring, as continuously as is necessary with respect to an industrial process, the streaming potential of a particle suspension or for measuring the streaming potential and/or the state of drainage of a particle suspension. The apparatus is adaptable for the simultaneous measurement of the streaming potential and the state of drainage. The method and the apparatus make possible substantially automatic measurements which to a high degree are exempt from disturbances, and the values of measurement obtained, which are proportional to the above-mentioned quantities, are usable immediately and automatically for controlling as desired the streaming potential and/or the state of drainage.

BRIEF DESCRIPTION OF THE DRAWINGS

The method and the apparatus of the invention will be explained in detail in the following specification with reference to the enclosed drawings, wherein.

DETAILED DESCRIPTION OF THE PREFERRED EMBODIMENTS

Figure 1:
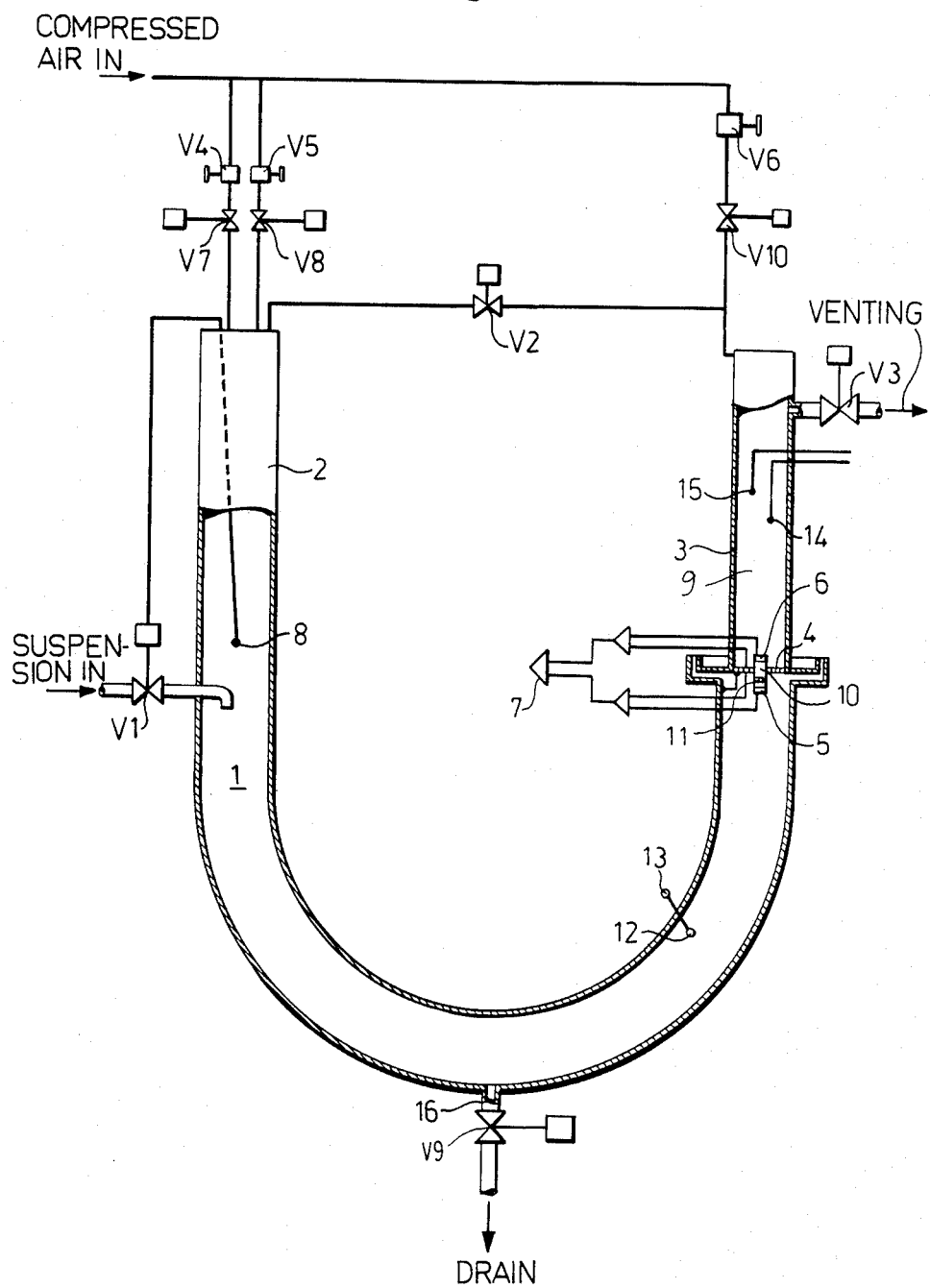
FIG. 1 diagrammatically and in section shows a first embodiment of the apparatus of the invention for measuring the streaming potential and/or the state of drainage of a particle suspension, and FIG. 2 diagrammatically and in section shows a second embodiment of the apparatus of the invention for measuring the streaming potential of a particle suspension.

Briefly, the first embodiment of the apparatus of the invention shown in FIG. 1 comprises a measuring vessel 1 in which is introduced a sample of the liquid suspension participating in an industrial process whose streaming potential or state of drainage are to be measured and controlled. The measuring vessel is connected to means, described below, for introducing thereinto the liquid suspension, for rinsing the measuring vessel and gauges for determining the required quantities of measurement etc. Measuring vessel 1, which has the shape of a U having vertical legs 2 and 3 the free ends of which are at the top, in one leg 3 has a screen plate 4 for collecting a pad of particles (not shown). An electrode 5, 6 is provided on each side of screen plate 4. These have a differential amplifier 7 connected thereto with relatively grounded screen plate 4 as a reference. The values of measurement are applied to a microcomputer programmed to control means for introducing the liquid suspension and for rinsing measuring vessel 1 and for starting measurements as required as well as for processing the collected values of measurement and computing and displaying in suitable units the streaming potential and, as the case may be, the drainage properties. Of course, the obtained results may be used to control directly the streaming potential or state of drainage of the suspension participating in the process monitored through the measurements.

A portion of the particle suspension the streaming potential or state of drainage of which is to be determined is supplied to one leg 2 of measuring vessel 1 via a valve V1. Measuring vessel 1 is filled to a level determined by a level sensor 8 in the leg 2 which is supplied with the particle suspension. Level sensor 8 is connected to valve V1 so that upon the filling limit, which substantially corresponds to the level of screen plate 4 in leg 3, having been reached valve V1 is caused to interrupt the supply of the particle suspension. A valve V2 in a conduit connecting leg 2 with a conduit through which, as will be explained below, leg 3 above screen plate 4 is supplied with compressed air, also is connected to level sensor 8 and has for its purpose to equalize the pressure between legs 2 and 3 of measuring apparatus 1 and is adapted to be closed upon the intended suspension column height having been reached. Thereby equal suspension column heights are obtained in the two legs 2, 3. The portion of leg 3 which is above screen plate 4 constitutes a measuring chamber 9 which preferably is detachable and which is vented by means of a valve V3 through which the measuring chamber may be communicated with the atmosphere. Of course, valve V3 is open during the filling sequence to permit the air displaced by the inflowing liquid to be vented to the atmosphere.

To permit measuring the streaming potential and/or state of drainage of a particle suspension a predetermined differential pressure now is to be created across screen plate 4, i.e. between measuring chamber 9 and the rest of the portions of U-shaped measuring apparatus 1.

Legs 2 and 3 are connected to a source of compressed air via pressure reducing valves V4, V5 and, respectively, V6. Valve V4 produces a relatively low, constant pressure, for instance 0.1 bar, while valve V5 produces a pressure which, while low, is substantially higher than the pressure produced by valve V4, for instance 0.5 bar. Valve V6 produces a relatively high pressure, for instance 3 bars. When a valve V7 between valve V4 and left leg 2 is opened the volume of air above the suspension in left leg 2 is pressurized to the pressure valve V4 is set to produce. The liquid column in leg 2 thereby is depressed and the liquid column in leg 3 is pushed upwardly against screen plate 4. The particles in the suspension are intercepted by screen plate 4 while the liquid cleared of the particles, the filtrate, rises in measuring chamber 9.

According the the invention the two measuring electrodes provided on each side of screen plate 4 are supported by an insulating body 10 provided substantially at the centre of screen plate 4. This body which preferably is made of a suitable plastics material, such as polytetrafluoro ethylene, extends through screen plate 4 and carries at the top end thereof the one of the two electrodes just mentioned which is above screen plate 4 in measuring chamber 9, electrode 6, and at the bottom end thereof the electrode below screen plate 4, electrode 5. Upon a few seconds having elapsed since the liquid commenced rising in measuring chamber 9, electrode 6 will have become completely submerged by the filtrate and a measurement of the voltage between electrodes 5 and 6 is carried out. The arrangement is such that the voltages between each electrode 5, 6 and screen plate 4 are measured separately whereupon both are supplied to differential amplifier 7. The measurement is repeated 4–6 times at intervals of about 10 milliseconds to preclude disturbances on account of a mains frequency of 50 Hz. The measurement results are recorded in the microcomputer memory.

Thereupon valve V7 between valve V4 and left leg 2 is closed while a valve V8 between valve V5 and left leg 2 is opened. Thereby the pressure of the air above the suspension column of left leg 2 is increased to the pressure produced by valve V5. This higher pressure is propagated through the liquid resulting in the differential pressure between the suspension below screen plate 4 in right leg 3 and the liquid above screen plate 4, i.e. in measuring chamber 9, rising. After a few seconds the voltage between electrode 5 and 6 is now again measured as per above and the measurement results are recorded in the microcomputer memory.

According to the invention an electrode 11 connected to screen plate 4 is also provided, electrode 11, in the embodiment being described, being positioned on insulating body 10 below screen plate 4, viz. for measuring the resistance between electrode 11 and screen plate 4. Thereby, a measure of the conductivity of the suspension may be obtained. Electrode 11 is caused to become operative upon the step of the process of measurement last described above having been carried out. The measure of the conductivity of the suspension thus now obtained is supplied to and recorded in the microcomputer memory. The temperature of the suspension is recorded at the same time by means of a temperature sensor, preferably a resistance thermometer 12, connected to a means 13 for converting resistance to voltage. The voltage obtained by means 13 is applied to and recorded in the microcomputer memory.

The differential pressure across screen plate 4 thereupon is reduced by valve V8 being closed and valve V7 opened. The voltage between electrodes 5 and 6 is now again measured as per above and the result is supplied to and recorded in the microcomputer memory.

The microcomputer now can compute the streaming potential of the particle suspension by subtracting the result of the measurements of the voltage between electrodes 5 and 6 carried out at the smaller differential pressure from the result of the measurements of the voltage between the electrodes carried out at the larger differential pressure. Thereby, the microcomputer may compute the streaming potential searched for which is possible by the microcomputer program taking into account the fact that the potential is proportional to the above quantities and by the fact that, as described above, the values in question having been supplied to and recorded in the microcomputer memory. Thus, the microcomputer obtains the conductivity of the suspension by computing it by means of the measure of the resistance obtained by electrode 11, the viscosity of the suspension by means of the temperature measurement, while the dielectric constant of the suspension is assumed to be of a non-variable value programmed into the computer.

On account of the fact that in the embodiment now being described screen 4 is grounded a large proportion of the disturbances which may affect the measurements described above are eliminated.

The differential pressure maintained across screen plate 4 by valves V4 and V7 causes the liquid level in measuring chamber 9 to continue rising. A pair of liquid level sensors provided in measuring chamber 9 above screen plate 4 now may be used for measuring the state of drainage, viz. a liquid level sensor 14 at a lower level and a liquid level sensor 15 at a higher level. Preferably, the two sensors, as well as level sensor 8, consist of rods of conductive metal connected to conductivity sensitive relays of known type. When the rising filtrate reaches the lower liquid level sensor 14 a time meter in the microcomputer is started, the time meter being stopped when the filtrate reaches upper liquid level sensor 15. From the time elapsed between the moment the filtrate reached lower liquid level sensor 14 and the moment the filtrate reached upper liquid level sensor 15, the time of drainage, and from suspension conductivity and temperature values previously measured and stored in the microcomputer memory as per above as well as from coefficients known by the expert and introduced into the microcomputer memory, the microcomputer now computes a quantity which is a measure of the state of drainage of the suspension or, if it is a suspension the particles of which completely or partly consist of cellulose fibres, its degree of beating or freeness.

The embodiment of the device according to the invention described above is arranged such that when the filtrate has reached the level of upper liquid level sensor 15 a rinsing cycle is activated by means of which measuring apparatus 1 is to be cleaned and prepared for the next measuring cycle. When the measuring cycle is initiated valves V3 and V7 are closed and valve V2 opened as well as a valve V9 provided in a drain 16 from the bottom of U-shaped measuring apparatus 1 whereupon a valve V10 is opened, the latter valve being provided in the compressed air conduit between the valve V6 which produces a relatively high pressure and the point at which the compressed air conduit is connected to leg 2 of measuring apparatus 1. Compressed air of a pressure determined by valve V6, for instance about 3 bars, now is supplied to the two legs 2 and 3 from above. Preferably, the air is introduced into leg 3 which contains measuring chamber 9 and screen plate 4 via a connection to the top end of leg 3 arranged to make the air flow tangentially into the measuring chamber. Thereby, the liquid therein is imparted a whirling motion and, since the connection is provided with a restriction which increases the velocity of the air and since measurement chamber 9 in the embodiment being described is of lesser diameter than the rest of the tube which forms U-shaped measuring apparatus 1, the liquid measuring chamber 9 is imparted an increased velocity of flow. On account of the fact that body 10 with electrodes 5, 6 and 11 is centrally positioned on screen plate 4 the vortex of liquid will not be disturbed by the electrode arrangement. The compressed air initially will force out the filtrate in measuring chamber 9 through screen plate 4 entraining the pad of particles on the bottom face of screen plate 4. Thereupon, and also partly simultaneously therewith, the suspension in the two legs 2 and 3 is forced downwardly in the legs and thence out through drain 16 having its valve V9 open. When measuring apparatus 1 has been completely emptied after a few seconds valves V10 and V9 are closed. Thereupon, valve V1 is opened and the next measuring cycle starts.

As is understood by the expert the apparatus described above may be used solely for measuring the streaming potential of a suspension or solely for measuring the state of drainage thereof or for measuring the above variables simultaneously or separately without compensating for temperature, conductivity etc.

In many situations and when only measuring the streaming potential of a suspension is of interest it may often be sufficient to carry out measurements without compensating, in the first place, for viscosity and conductivity. Thus, it has been found that in many cases acceptable results are obtainable using a simplified—and hence cheaper—method of measuring according to which only one of the pressures is altered so that the pressure ratio is always zero. A simplified apparatus for carrying out this simplified method of measurement is shown in FIG. 2.

Figure 2:
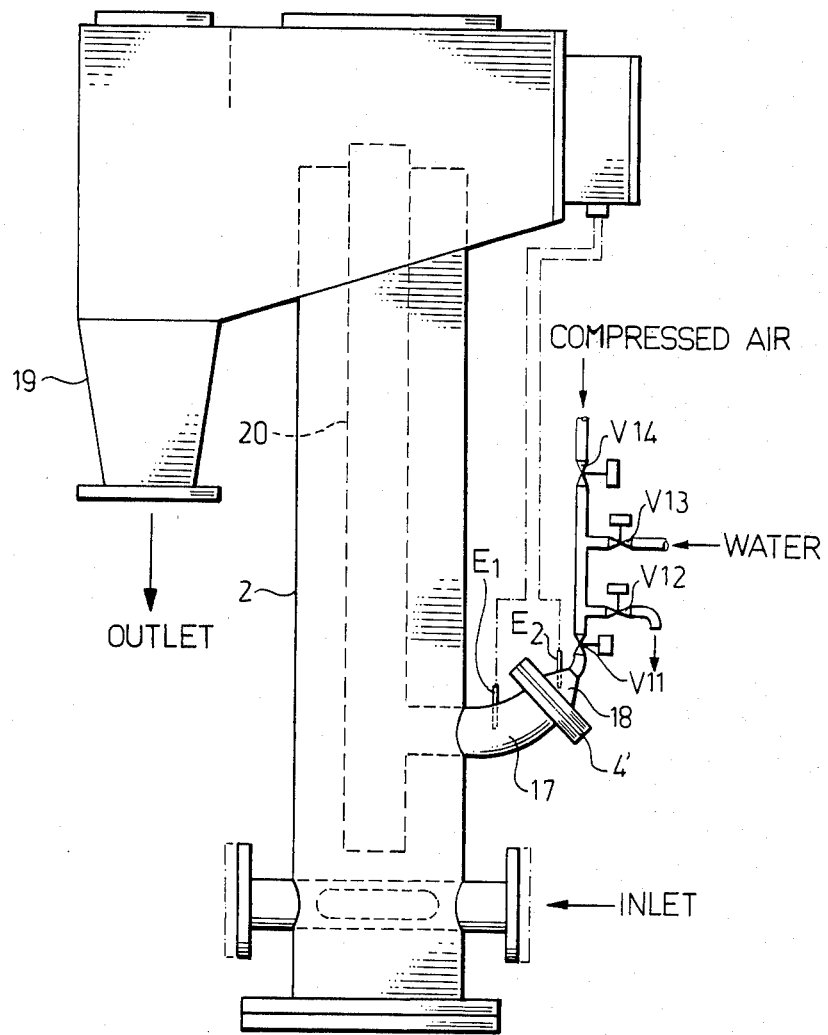

The arrangement of FIG. 2 for measuring only the streaming potential of particle suspensions comprises a pair of metal electrodes $E_1$ and $E_2$ provided on each side of a screen plate 4'. The latter is provided adjacent the outer end of a conduit 17 the end portion of which outside screen plate 4' constitutes a measuring chamber 18. Conduit 17 is connected to the apparatus 19 wherein proceeds the process the measurements relate to, viz. downstream an inlet to apparatus 19 and via a means by which the particle suspension is caused to exert a static pressure upon the side of screen plate 4' facing away from measuring chamber 18. This means for instance may consist of a vessel having an air cushion or, preferably, a level vessel 20 of a function and nature evident from Swedish patent publication No. 334 493 the contents of which is included herein by way of reference.

The two electrodes $E_1$ and $E_2$ preferably are circular and positioned in conduit 17 with their axes substantially parallel with the local axis of the conduit. Thereby, the automatic cleaning of the electrodes by means of rinsing liquid supplied tangentially to the conduit is facilitated.

Measuring chamber 18 may be communicated with the atmosphere by means of valves V11 and V12 and with pressurized water and air by means of valves V13 and V14, respectively. When measuring chamber 18 is filled with filtrate the closure of valve V11 results in equal pressures being produced on both sides of screen plate 4'. The difference between the pressures on either side of screen plate 4' hence is zero. On the other hand, when valves V11 and V12 are open atmospheric pressure will prevail on the measuring chamber side of screen plate 4', and hence the differential pressure will then be determined by level vessel 20 (or the air cushion vessel). If now the voltage between electrodes $E_1$ and $E_2$ is measured on one hand with valve V11 closed and on the other hand with the valve open and the two valves of measurement are subtracted from each other a differential voltage constituting a measure of the electric streaming potential of the suspension will be obtained.

In an imaginary initial situation valves V11 and V12 now are assumed open and valves V13 and V14 closed. After a predetermined space of time valve V11 is closed and the voltage between electrodes $E_1$ and $E_2$ is recorded, preferably in a microcomputer memory. Upon a further predetermined space of time having elapsed valve V11 is opened whereupon the voltage at the selected differential pressure is recorded. Thereupon valve V11 is again closed and the voltage is again measured. If the voltage at the two measurements without differential pressure exhibits a difference larger than a predetermined value valve V11 is again opened and closed and the measurements are repeated until stability has been reached. Thereupon valve V11 is opened, valve V12 closed and valve V14 opened for admitting compressed air into measuring chamber 18 as is valve V13 for admitting water to clean the measuring chamber and screen plate 4'. From the arrangement shown in FIG. 2 it is evident that measuring chamber 18 is supplied with a mixture of compressed air and water, viz. such that the compressed air is mixed with water droplets. Measuring chamber 18 preferably is substantially cylindrical and when the mixture of compressed air and water is supplied thereto tangentially the optimum cleaning effect is obtained. After a few seconds first valve V13 and then valve V14 are closed whereupon valve V12 is opened for drainage. Valve V11 remains open and a new measuring cycle is started.

As has already been hinted at a microcomputer preferably is provided for controlling the valves and processing the collected values of measurement.

I claim:

1. A method of simultaneously and continuously measuring both the streaming potential and the rate of drainage of a particle suspension, comprising the steps of:

(a) introducing a particle suspension into a measuring vessel (1), (b) alternately subjecting the particle suspension, to two different, predetermined, relatively low but significantly dissimilar pressures to force the suspension through a screen (4) transversely interposed across a flow path (3) defined by the vessel such that the screen intercepts particles in the suspension, (c) simultaneously with step b), venting the vessel above the screen, (d) measuring the voltage across the screen at each of the two pressures, (e) subtracting the voltage measured at a lower one of the pressures from the voltage measured at a higher one of the pressures, (f) measuring the resistance of the suspension and determining the conductivity therefrom, (g) measuring the temperature of the suspension and determining the viscosity therefrom, (h) computing the streaming potential of the suspension from the values of the conductivity and viscosity of the suspension and from the differential pressure between the upstream side of the particles collected on the bottom side of the screen and the downstream side of the screen as determined by the voltage measurements as well as from a predetermined suspension dielectric constant, (i) measuring the velocity of flow of filtrate downstream of the screen, and (j) computing the rate of drainage of the suspension from the value of the velocity of flow of filtrate at a known differential pressure between the upstream and downstream sides of the screen.

2. The method of claim 1, wherein for measuring only the streaming potential of the particle suspension the two pressures are selected to be, on one hand, an arbitrary but pre-selected pressure determined by a level vessel (20) or an air cushion, and, on the other hand, the atmospheric pressure, the higher differential pressure being constituted by the difference between the arbitrary pressure and the atmospheric pressure and the lower differential pressure being selected to be zero, the measurements of the resistance of the suspension and the temperature thereof being omitted and the streaming potential of the particle suspension being determined solely on the basis of the difference between two electrodes ($E_1$, $E_2$) provided on each side of the screen (4') with, on one hand, the measuring vessel open to the atmosphere, and, on the other hand, the measuring vessel open to the particle suspension.

3. The method of claim 1, wherein the predetermined, relatively low pressures to which the suspension is alternately subjected are selected to be of the order of 0.1 and 0.5 bar, respectively.

4. The method of any one of claims 1–3, wherein after each completed streaming potential or rate of drainage measurement the vessel is rinsed by the suspension and the filtrate is caused to flow towards a drain under a pressure on the order of 3 bars, the filtrate being caused to flow through the screen (4) counter to its direction during the measurements.

5. The method of claim 4, wherein the sequences of suspension introduction, pressure variations, measurements and rinsing are monitored and controlled by a microcomputer which on the basis of a pre-selected program and data obtained from the sequences of measurements as well as pre-stored quantities is caused to compute the results of the measurements, and controlling the streaming potential and the rate of drainage of the suspension in accordance with the computed measurement results.

6. An apparatus for simultaneously and continuously measuring both the streaming potential and the rate of drainage of a particle suspension introduced into a measuring vessel (1), characterized by: a screen plate (4) adjacent a downstream end of the vessel and extending transversely thereacross, a detachable, vented measuring chamber (9) located on the downstream side of the screen, valve means (V4, V5, V7, V8) for alternately subjecting the suspension upstream of the screen plate to two predetermined, relatively low but substantially different pressures, electrodes (5, 6) provided on each side of the screen plate for determining at the two different pressures the voltage between the particle suspension on the upstream side of the screen plate and filtrate on the downstream side thereof, means (12, 13) for measuring the temperature of the suspension, a further electrode (11) associated with the screen plate for measuring the resistance between the electrode and the screen plate, and liquid level sensors (14, 15) provided in the measuring chamber and located at different levels above the screen plate for determining the velocity of flow of the filtrate from the time the filtrate requires to rise from the level of the lower liquid level sensor (14) to the level of the upper liquid level sensor (15).

7. The apparatus of claim 6, wherein the measuring vessel (1) has vertical legs (2, 3), free ends of which are at the top and of which one leg (2) is adapted to be supplied with a sample of the particle suspension, and of which the other leg (3) adjacent the top end thereof is provided with said substantially horizontal screen plate (4) defining from the rest of the measuring vessel the measuring chamber (9) located above the screen plate and supporting substantially at the centre thereof a body (10) extending through the screen plate and individually carrying at its opposite ends the electrodes (5, 6) located on either side of the grounded screen plate and also the further electrode (11) associated with the screen plate, the electrodes located on each side of the screen plate being connected to a differential amplifier (7).

8. The apparatus of claim 7, wherein said valve means (V4, V5, V7, V8) are provided in a pair of conduits branched off from a conduit connected to a source of compressed air, both branced off conduits being connected to the measuring vessel leg (2) to which the particle suspension is supplied, of which valve means a first one (V4) is located in one of the branched off conduits and is adapted to produce a relatively low pressure of the order of 0.1 bar, a second valve means (V7) being located in the same branched off conduit, between the first valve means and the measuring vessel leg and adapted to selectively open or close the connection between the first valve means and the measuring vessel, a third one (V5) being located in the other one of the branched off conduits and adapted to produce a relatively low but substantially higher pressure than the pressure produced by the first valve means, preferably of the order of 0.5 bar, a fourth value means (V8) being located in the same branched off conduit as the third valve means and between the latter and the measuring vessel leg and adapted to selectively open or close the connection between the third valve means and the measuring vessel leg.

9. The apparatus of claim 7 or 8, wherein a level sensor (8) is located in the measuring vessel leg (2) supplied with the particle suspension to sense a level of the particle suspension introduced into the measuring vessel leg substantially corresponding to the level of the screen plate (4) located in the other measuring vessel leg and, when the said level is being sensed, to actuate a valve (V1) located in a supply conduit to the measuring vessel (1) for discontinuing the supply of particle suspension, the level sensor being associated with a valve (V2) provided in a conduit connnecting the leg which is supplied with the suspension with the other leg (3) to equalize the pressure between the two legs of the measuring vessel, the last-mentioned valve being adaped to be closed when the intended particle suspension level has been reached so that the same suspension column height is maintained in the two legs.

10. The apparatus of claim 8, wherein a conduit is connected to the source of compressed air, said conduit being connected to the upper end of the measuring chamber (9) in such a manner that it opens tangentially into the measuring chamber and with a restriction, the measuring chamber being of smaller diameter than the rest of the measuring vessel, the conduit having a valve (V6) producing a relatively high pressure of the order of 3 bars, and between the latter and the point where the conduit is connected to the measuring chamber a valve (V10) is disposed to selectively open or close the connection between the source of compressed air and the measuring chamber via the valve adapted to produce a relatively high pressure, a conduit connected between the measuring chamber legs to equalize the pressure between the two legs of the measuring vessel so that the measuring vessel may be rinsed under pressure simultaneously from the upper ends of the two measuring vessel legs, and a valve-controlled drain (16, V9) being provided at the lowermost point of the vessel.

11. The apparatus of claim 6 wherein all of the valves, sensors, and electrodes are connected to a microcomputer for controlling the operation of the valves in accordance with data transmitted to the microcomputer and a preselected program which, in addition to control the operation of the valves also is adapted to compute the results of measurement with the aid of said data and prestored quantities, the microcomputer being connected to a device for controlling the streaming potential and rate of drainage of the suspension participating in the process on the basis of the computed results of measurements.

12. An apparatus for measuring the streaming potential of a particle suspension, comprising: a measuring vessel including a conduit (17) having adjacent an outer end portion thereof a screen plate (4') defining a measuring chamber (18) formed by the end portion and having an inner end thereof connected to an apparatus (19) in which a process the measurements relate to take place via a level vessel (20) or a vessel having an air cushion such that the particle suspension is caused to exert a static pressure on the side of the screen plate facing away from the measuring chamber, a pair of circular metal electrodes ($E_1$, $E_2$) provided in the conduit, with their axes parallel with the axis of the conduit, on each side of the screen plate, and valves (V11, V12, V13, V14) for selectively communicating the measuring chamber with the atmosphere, with water and with air under pressure.

* * * * *